(12) United States Patent
Kwong et al.

(10) Patent No.: US 8,211,696 B2
(45) Date of Patent: Jul. 3, 2012

(54) METHOD USEFUL FOR HCV RNA898 INFECTION

(75) Inventors: Ann Kwong, Cambridge, MA (US); Randal Byrn, Wayland, MA (US); Lola M. Reid, Chapel Hill, NC (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/013,758

(22) Filed: Jan. 25, 2011

(65) Prior Publication Data

US 2011/0229874 A1 Sep. 22, 2011

Related U.S. Application Data

(62) Division of application No. 10/109,298, filed on Mar. 27, 2002, now Pat. No. 7,879,606.

(60) Provisional application No. 60/279,174, filed on Mar. 27, 2001.

(51) Int. Cl.
 *C12N 5/071* (2010.01)

(52) U.S. Cl. ...................................................... 435/370

(58) Field of Classification Search ................... 435/370
See application file for complete search history.

(56) References Cited

U.S. PATENT DOCUMENTS

| | | | |
|---|---|---|---|
| 5,529,920 | A | 6/1996 | Cole et al. |
| 5,576,207 | A | 11/1996 | Reid et al. |
| 5,789,246 | A | 8/1998 | Reid et al. |
| 5,849,686 | A | 12/1998 | Kuberasampath et al. |
| 6,069,005 | A | 5/2000 | Reid et al. |
| 6,127,116 | A | 10/2000 | Rice et al. |
| 6,146,889 | A | 11/2000 | Reid et al. |
| 6,242,252 | B1 | 6/2001 | Reid et al. |
| 7,183,095 | B2 | 2/2007 | Dasgupta et al. |
| 2001/0023073 | A1 | 9/2001 | Bhatia et al. |
| 2001/0043919 | A1 | 11/2001 | Reid et al. |
| 2002/0016000 | A1 | 2/2002 | Reid et al. |
| 2002/0039786 | A1 | 4/2002 | Reid et al. |
| 2002/0187133 | A1 | 12/2002 | Kubota et al. |
| 2004/0167067 | A1 | 8/2004 | Griggs et al. |

FOREIGN PATENT DOCUMENTS

| | | |
|---|---|---|
| EP | 1421222 | 5/2004 |
| JP | 2004-537279 A | 12/2004 |
| WO | WO 93/03142 | 2/1993 |
| WO | WO 95/13697 | 5/1995 |
| WO | WO 99/67362 A1 | 12/1999 |
| WO | WO 00/34507 | 6/2000 |
| WO | WO 00/43498 | 7/2000 |
| WO | WO 01/53462 | 7/2001 |
| WO | WO 02/28997 | 4/2002 |
| WO | WO 02/29012 | 4/2002 |
| WO | WO 02/072776 | 9/2002 |

OTHER PUBLICATIONS

Aparicio, P. et al. Isolation and characterization of (gamma alpha) CD4+ T cell clones derived from human fetal liver cells. *Journal of Experimental Medicine*, vol. 170 pp. 1009-1014, (1989).

Carloni, G. et al., "Susceptibility of human liver cell cultures to hepatitis C virus infection," *Arch. Virol*, 8, pp. 31-39 (1993).

Chessebeuf, M. et al., "Rat liver epithelial cell cultures in a serum-free medium: primary cultures and derived cell lines expressing differentiated functions," In Vitro, 20(10), pp. 780-795 (1984).

Clarysse, C. et al., "In vitro assays for drug testing: continuous cell lines," *Acta Gastro-Enterologica Belgica*, 63, pp. 213-215 (2000).

Fournier et al., "In vitro infection of adult normal human hepatocytes in primary culture by hepatitis C virus", *Journal of General Virology*, vol. 79, pp. 2367-2374 (1998).

Gilbert, S., Developmental Biology, 6th Edition (2000).

Harlow et al. *Antibodies: A Laboratory Manual* (1988) Cold Spring Harbor Laboratory, pp. 349, 406-407; LSAB2 kit of DAKO Corporation.

Iacovacci, S. et al., "Replication and multiplication of hepatitis C virus genome in human foetal liver cells," Res. Virol. 144, pp. 275-279 (1993).

Ito, T. et al., "Cultivation of hepatitis C virus in primary hepatocyte culture from patients with chronic hepatitis C results in release of high titre infectious virus," Journal of General Virology, vol. 77, pp. 1043-1054 (1996).

Kubota, H. et al., "Clonogenic hepatoblasts, common precursors for hepatocyctic and biliary lineages, are lacking classical major histocompatibility complex class 1 antigen," *PNAS*, 97(22), pp. 12132-12137 (2000).

Lacovacci, S. et al., "Molecular characterization and dynamics of hepatitis C virus replication in human fetal hepatocytes infected in vitro," *Hepatology*, 26(5) pp. 1328-1337 (1997).

Levesque, *Use of serum-free media to minimize apoptosis of chronic lymphocytic leukemia cells during in vitro culture*, Leukemia 2001, pp. 1305-1307.

*Methods for Tissue Engineering*, Ed. Robert Lanza, Academic Press, NY (2002), pp. 151-202.

Morrica, A. et al., "Susceptibility of human and non-human cell lines to HCV infection as determined by the centrifugation-facilitated method," *Journal of Virological Methods*, 77, pp. 207-215 (1999).

Ochiya, T. et al. An in vitro system for infection with hepatitis B virus that uses primary human fetal hepatocytes. *PNAS*, vol. 86 pp. 1875-1879, (1989).

Rumin et al., "Dynamic analysis of hepatitis C virus replication and quasispecies selection in long-term cultures of adult human hepatocytes infected in vitro", *Journal of General Virology*, vol. 80, pp. 3007-3018 (1999).

Salas-Prato, M. et al., "Attachment and multiplication, morphology and protein production of human fetal primary liver cells cultured in hormonally denned media," *In Vitro Cellular & Developmental Biology*, 24(3), pp. 230-238 (1988).

Seipp, S. et al., "Establishment of persistent hepatitis C virus infection and replication in vitro," *Journal of General Virology*, 78, pp. 2467-2476(1997).

Susick et al., "Hepatic Progenitors and Strategies for Liver Cell Therapies for Liver Cell Therapies," *Ann. NY Acad. Sci.*, 944:398-419(2001).

(Continued)

*Primary Examiner* — Jon E. Angell

(74) *Attorney, Agent, or Firm* — Ropes & Gray LLP; James F. Haley, Jr.; Yang Xu

(57) ABSTRACT

The present invention provides compositions comprising cells that can effectively produce HCV after HCV infection, compositions for culturing the cells, methods for making the composition and methods for infecting the cells in the composition with HCV. The present invention also provides methods for assaying HCV production and methods for evaluating compounds that affect the production of HCV.

12 Claims, 5 Drawing Sheets

OTHER PUBLICATIONS

*Teratocarcinomas and Embryonic Stem Cells: A Practical Approach*, ed. Robertson, E.J. (IRS, Oxford), pp. 71-112, (1987).

Yoo, B.J.et al., "Transfection of a differentiated human hepatoma cell line (Huh7) with in vitro-transcribed hepatitis C virus (HCV) RNA and establishment of a long-term culture persistently infected with HCV," *Journal of Virology*, 69(1), pp. 32-38 (1995).

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ccatgaatca ctcccctgtg                                          20

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccggtcgtcc tggcaattc                                                       19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagggtagtc gtcagtggtt cg                                                   22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcctctgca gcaccctatc                                                      20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cctggaggct gcacgacact ca                                                   22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ccctcgtcca cgtggcatct cga                                                  23
```

METHOD USEFUL FOR HCV RNA898 INFECTION

This application is a divisional of U.S. patent application Ser. No. 10/109,298, filed Mar. 27, 2002 (now U.S. Pat. No. 7,879,606), which application claims benefit of and priority from U.S. Provisional Patent Application 60/279,174, filed Mar. 27, 2001. All the prior applications are incorporated herein by reference in their entirety.

BACKGROUND OF THE INVENTION

Although Hepatitis C Virus (HCV) replicates robustly in infected human, a robust method of growing the virus in cultured cells has not been perfected. When infectious serum is used to infect cultured human liver cells in vivo, only small amounts of HCV are replicated which are only detectable by reverse transcriptase polymerase chain reaction (RT-PCR).

Attempts to infect cultured cells with HCV have been reported for peripheral blood mononuclear cells, human B and T cell lines, human hepatocyte lines, and primary human fetal and adult cells. However, the results reported to date have been disappointing. Often viral replication is so low that HCV produced from an infected population of cells can only be detected, if at all, with RT-PCR and then only low numbers of copies of HCV RNA can be observed. Further, the viral production is sporadic and not reproducible from well to well on the same or different days with the same virus and cells. Further still, it takes several days, even as much as a month after administering the virus to observe the peak of infection, e.g., Iacovacci et al., *Hepatology* 26(5):1328-1337 (1997). These problems frustrate the identification and rapid screening of compounds that may be useful for treating patients suffering from HCV and/or for research relating to HCV infection.

Thus, there is a need for a method for infecting and replicating HCV in cell culture. There is also a need for quick and efficient methods for determining compounds which inhibit HCV production in culture. This application solves these problems by providing compositions comprising cells that can effectively reproduce HCV, methods for making the composition of cells, media for culturing cells, methods for infecting cells with HCV, methods for assaying HCV infection, and methods for evaluating the ability of a compound to affect the production of an HCV using the compositions and methods of this invention.

SUMMARY OF THE INVENTION

The present invention provides methods for making compositions comprising high HCV producing culture cells. The present invention provides compositions comprising cell mixtures comprising cells from the liver of a human aged three months or older after conception which can be efficiently and effectively infected with an HCV. The present invention also provides compositions comprising cells prepared by the methods of this invention. In one embodiment, the compositions of this invention comprise cell mixtures comprise cells that express alpha fetoprotein, cells that express albumin, cells that express glycophorin, but are substantially free of cells that express CD34 protein. In another embodiment of this invention, the cells in the cell mixture can pass through a filter about 40 microns in size. In another embodiment of this invention, the composition is used in conjunction with or further comprises a feeder cell. In yet another embodiment of this invention, the feeder cell is a STO(Reid-99) cell.

The present invention provides compositions for culturing cells. In one embodiment of this invention, the compositions for culturing cells comprise: serum-free media comprising calcium, free fatty acids (FFA), high density lipoprotein (HDL), nicotinamide, trace elements, epidermal growth factor (EGF), insulin, transferrin and hydrocortisone. According to another embodiment of this invention, the above compositions do not comprise low density lipoprotein. According to another embodiment of this invention, the composition further comprises any one, combination, or all of the following ingredients: glucagon, liver growth factor, ethanolamine and thyrotropin releasing factor.

The present invention provides methods for infecting a cell mixture by administering an HCV to compositions of this invention. According to one embodiment of this invention, the HCV is RNA898. In another embodiment of this invention, the HCV virus is initially incubated with the composition (innoculum) for about 24 hours at about 37 degrees C. in a volume of about 0.52 ml per cm$^2$ prior to washing the cells in the composition or replacing the innoculum with cell culture media.

The present invention provides a method for assaying HCV infection by incubating a composition of this invention with a feeder cell, contacting the cells in the composition with an HCV; and measuring the HCV associated with the cells and/or media in which the cells are cultured.

Further, the present invention provides a method for evaluating the ability of a compound to affect the production of HCV, i.e, affect the ability of the composition of cells to produce more HCV, comprising the steps of incubating a composition of this invention with a feeder cell, contacting the cells in the composition with an HCV virus and administering the compound before or after contact with HCV. In one embodiment, the method is used to screen for cells that inhibit HCV production. In a further embodiment, the method is used to screen a plurality of compounds simultaneously for their ability to inhibit HCV production.

In another embodiment, presence of HCV is determined by measuring the quantity of HCV RNA by reverse-transcriptase polymerase chain reaction (RT-PCR). In one embodiment, the HCV RNA in the sample is compared to an amount of RNA from a second virus that is used as an internal control. In a further embodiment, the second virus is the Bovine Viral Diarrhea Virus ("BVDV").

DETAILED DESCRIPTION OF THE INVENTION

Figure 1:
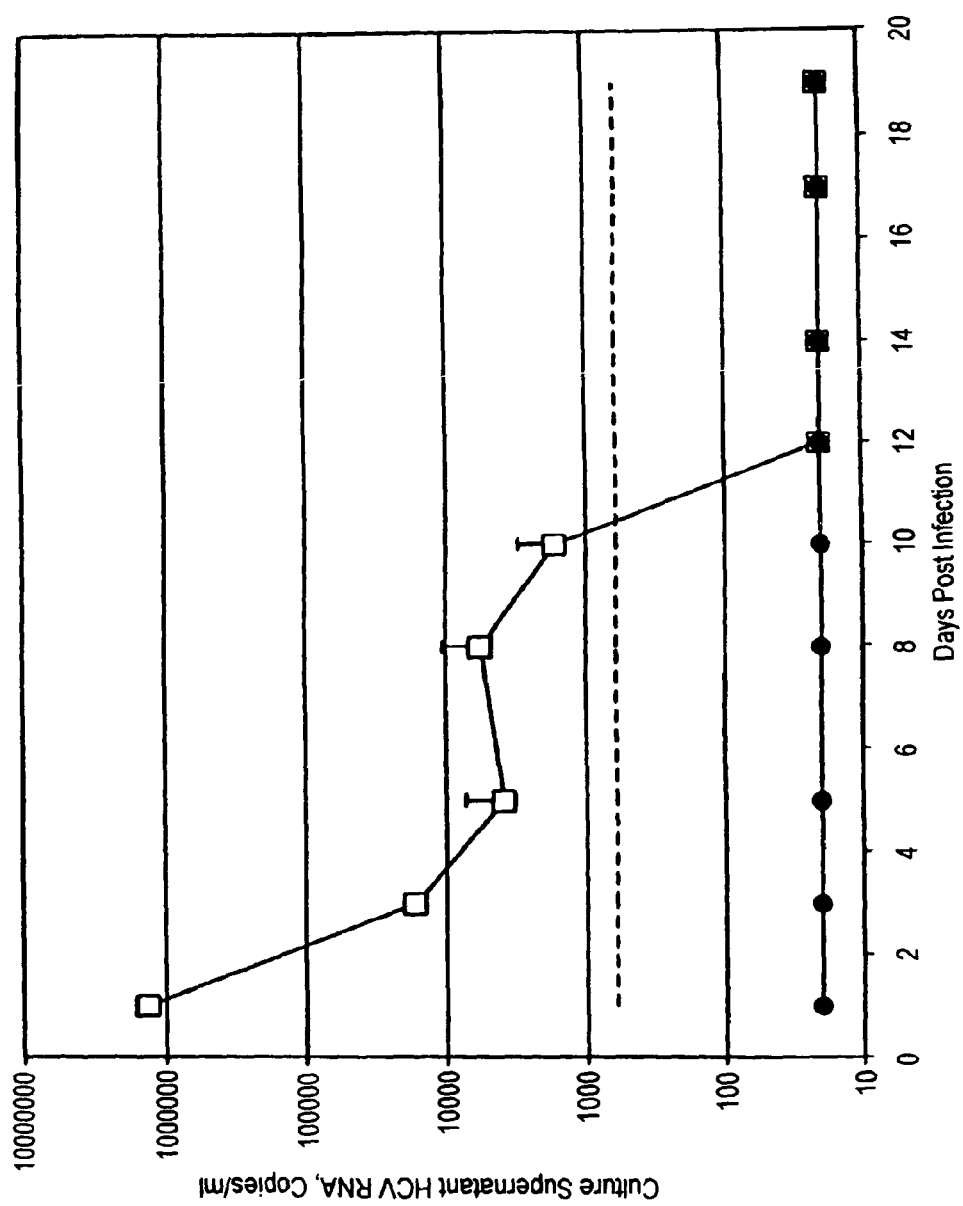
FIG. 1 depicts a time course analysis of the infection of human fetal liver cells following infection with RNA898 (-□-) or no serum control (●) as measured by levels of HCV RNA present in culture supernatants. The limit of quantitation (----LOQ) of the RT-PCR assay for supernatant samples was 600 HCV RNA copies/sample. The mean HCV RNA/ml values, and their standard deviation, from triplicate cultures are presented.

A composition of this invention comprises a cell mixture comprising cells released from the liver of a human aged three months or older after conception. According to one embodiment, the human is aged between and including three months after conception up to 1 year after birth. In another embodiment of this invention, the human is aged three to six months after conception. In another embodiment, the human is aged between 18 to 22 weeks after conception. In one embodiment of this invention, the cells comprise fetal liver and hematopoietic cells. According to one embodiment of this invention, the liver and hematopoietic cells can express alpha fetoprotein, albumin and/or glycophorin. According to one preferred embodiment, if the human is an adult, the human liver is healthy.

According to another embodiment, a composition of this invention comprises cells that express alpha fetoprotein, cells that express albumin, and cells that express glycophorin, but is substantially free of cells that express CD34 protein. The cells of the cell mixture are immunostainable with antibodies specifically directed against alpha fetoprotein, albumin or glycophorin, but the cell mixture is substantially free of cells that are immunostainable with an antibody specifically directed against CD34 protein. According to this invention, the term "substantially free of cells that express CD34 protein" means that the cells in the cell mixture display little or no observable immunostaining with the CD34 antibody when immunobinding is detected using an alkaline phosphatase-dye detection system (e.g., Harlow et al., *Antibodies: A Laboratory Manual* (1988) Cold Spring Harbor Laboratory, pp. 349, 406-407; LSAB2 kit of DAKO Corporation). According to one embodiment of the composition of this invention, less than 2% of the cell population of the cell mixture would be stainable with an anti-CD34 specific antibody. According to another embodiment, less than 1% of the cell population of the cell mixture would be stainable with anti-CD34 specific antibody.

The present invention includes a composition comprising cells which are significantly better host cells for the infection and replication of the HCV virus, RNA898 (hereinafter, "RNA898"). RNA898 was deposited on Mar. 27, 2001, in the American Type Culture Collection ("ATCC"), 10801 University Boulevard, Manassas, Va. 20110-2209) (ATCC Deposit No: PTA-3237) under the conditions of the Budapest Treaty. According to one embodiment, a composition of this invention is capable of producing more than about 5,000 copies; more than about 10,000 copies; or more than about 50,000 copies of hepatitis C viral RNA in the media seventy-two hours after administering the virus if there are $4 \times 10^5$ cells in the composition. For example, a composition prepared according to the methods of this invention and assayed according to the methods described in Examples 2 and 4 would be capable of producing more than about 5,000, more than about 10,000 copies, or more than about 50,000 copies of hepatitis C viral RNA in the media seventy-two hours after administering the virus.

One of skill in the art would readily understand that if the number of cells in the composition were greater than $4 \times 10^5$ cells, then the total number of copies of viral RNA being produced would be increased by an amount commensurate with the increased number of cells in the composition. Similarly, one of skill in the art would readily understand that if the number of cells in the composition were smaller than $4 \times 10^5$ cells, then the total number of copies of viral RNA being produced would be decreased by an amount commensurate with the increased number of cells in the composition. Accordingly, compositions comprising less or more than $4 \times 10^5$ cells which would proportionally produce the same number of copies of HCV RNA are contemplated. The compositions according to this invention are capable of producing 5,000-55,000 copies of HCV RNA; 10,000-55,000 copies of HCV RNA and 25,000-55,000 copies of HCV RNA seventy-two hours after administration of the virus to the composition.

Examples of antibodies that are useful for immunostaining according to this invention are known in the art. For example, the anti-alpha fetoprotein antibodies from DAKO Corporation, Carpinteria, Calif., the anti-glycophorin antibodies (32591) from PharMingen, San Diego, Calif., the anti-human CD34 antibodies (34371A) from PharMingen, San Diego, Calif. and the anti-albumin antibodies (YM5024) from Accurate Chemical Corp., Westbury, N.Y. can be used.

In another embodiment of this invention, the cell mixture in a composition of this invention can pass through a filter about 40 microns in size.

In one embodiment of this invention, the compositions of this invention are used in conjunction with or further comprise feeder cells. Feeder cells provide extracelluar matrix and diffusible factors such as growth factors. In one embodiment, the feeder cell has little or no ability to be infected with HCV. In another embodiment, the feeder cells are fibroblast cells. In another embodiment, the feeder cells are embryonic mesenchymal fibroblast cells.

Examples of feeder cells according to this invention are mouse embryo fibroblasts (MEF) such as STO cells and rat embryo fibroblasts (REF), e.g, Brigid Hogan et al., *Manipulating The Mouse Embryo: A Laboratory Manual,* 2nd ed. Plainview, N.Y.: Cold Spring Harbor Laboratory Press, 1994; Robertson, E. J. (1987) *Teratocarcinomas and Embryonic Stem Cells: A Practical Approach*, ed. Robertson, E. J. (IRS, Oxford), pp. 71-112. STO(Reid-99) cells are one type of feeder cells that are useful. STO(Reid-99) cells were deposited on Mar. 27, 2001, in the American Type Culture Collection, 10801 University Boulevard, Manassas, Va. 20110-2209 under the conditions of the Budapest Treaty (ATCC Deposit No: PTA-3236). Methods for culturing and maintaining feeder cells are known in the art. See, for example, in *Methods for Tissue Engineering*, Ed. Robert Lanza, Academic Press, NY (2002), pp. 151-202.

The feeder cells can be growth arrested according to methods known in the art. For example, STO cells can be allowed to adhere for 2-48 hours on a cell culture plate. Next, the medium in which the STO cells are incubating would be removed and replaced with medium containing 2 ug/ml Mitomycin C. Then, the STO cells would be incubated at about 37 degrees C. for about 2 hours. After the incubation, the medium containing the Mitomycin C would be removed. The cells would be washed twice, and then the STO cell cultures would be maintained from 0-48 hours before addition of the cell mixtures of this invention.

The cell mixture of the compositions according to this invention can be prepared according to the steps that comprise:
 a. dissecting a liver of a human aged three months or older after conception in a buffer comprising EGTA;
 b. incubating the dissected liver in a buffer comprising collagenase to separate cells from the liver;
 c. removing objects about 40 micron or larger from the separated cells;
 d. removing red blood cells from the cell separated cells;
 e. resuspending the cells of step (d) in a serum-free media comprising 0.1 mM to 0.6 mM calcium, bovine serum albumin, free fatty acids (FFA), high density lipoprotein (HDL), nicotinamide, trace elements, epidermal growth factor (EGF), insulin, transferrin and hydrocortisone; and
 f. culturing the cells in the serum-free media of step (e).

The media of step (e) or (f) can optionally further comprise any one, combination or all of glucagon, liver growth factor, ethanolamine and thyrotropin releasing factor. In one embodiment, the media further comprises glucagon, liver growth factor, ethanolamine and thyrotropin releasing factor. In another embodiment, the media does not comprise low density lipoprotein (LDL).

In one embodiment, the EGTA buffer comprises 0.1 mM to 1.0 mM of ethylene glycol bis(β-aminoethyl ether)-N,N,N',N'-tetraacetate (EGTA). In another embodiment of this invention, the EGTA concentration is 0.5 mM.

In one embodiment, the collagenase buffer comprises 0.1 to 5.0 mg/ml of collagenase. In another embodiment of this invention, the concentration of the collagenase is 2 mg/ml.

The size exclusion step according to this invention is meant to remove objects such as tissue, debris and aggregates of cells which cannot pass through a filter of about 40 microns in size. Thus, for example, the use of filters approximately 40 microns in size up to 100 microns in size and other methods for removing debris greater than 40 microns in size are contemplated. In one embodiment, the filtration step removes objects that cannot pass through a filter that is greater than about 40 microns in size. Examples of filters according to this invention include nylon filters (e.g., "Cell strainer," from Falcon (catalogue nos. 2034, 2350 or 2360)).

The methods of preparing compositions of this invention include the step of removing red blood cells from the cell mixture. It should be understood that the red blood cells can be removed at any stage during the preparation process after the cells are separated from the liver. Methods for removing red blood cells are known in the art. According to one embodiment of the invention, the red blood cells are removed by successive low speed spins in a centrifuge. For example, the separated cells that were passed through the filters can be spun at 50×g (450 rpm) for 4 minutes, the cell pellet can be resuspended and the same process repeated several times.

Primary cells, cell lines and tissues of animals or humans can be cultured with a media of this invention. In one embodiment, the culture media comprises serum-free media, calcium, FFA, HDL, nicotinamide, trace elements, EGF, insulin, transferrin and hydrocortisone. According to another embodiment, the culture media can further comprises any one, combination or all of the following ingredients: glucagon, liver growth factor, ethanolamine and thyrotropin releasing factor. In a further embodiment, the culture media does not comprise low density lipoprotein (LDL).

After preparing a cell mixture according to the above process the cells should be cultured in a media suitable for sustaining the cells and, if necessary, the feeder cells. According to one embodiment of this invention, the media is optimized for a cell mixture that is to be used in an HCV infection. One media useful for this purpose comprises serum free media (e.g., (Dulbecco's modified Eagle's medium (DMEM)) comprising calcium, bovine serum albumin (BSA), free fatty acids (FAA), high density lipoprotein (HDL), nicotinamide, trace elements, epidermal growth factor (EGF), insulin, transferrin, hydrocortisone and optionally, and any one, combination or all of the following ingredients: glucagon, liver growth factor, ethanolamine, and thyrotropin releasing factor. According to one embodiment of this invention, the culturing media does not comprise low density lipoprotein (LDL).

In one embodiment, the concentration of calcium in the culturing media is between 0.1 mM to 0.6 mM. In another embodiment, the calcium concentration is approximately 0.5 mM. In one embodiment, the concentration of the BSA is 500 ug/ml. In another embodiment, the concentration of the nicotinamide is 5 mM. In one embodiment, the concentration of the insulin is 10 ng/ml. In one embodiment, the concentration of the free fatty acids is 7.6 uEq/L. In one embodiment, the concentration of EGF is 100 ng/ml. In one embodiment, the concentration of the liver growth factor is 20 ug/ml. In one embodiment, the concentration of the ethanolamine is $10^{-6}$M. In one embodiment, the concentration of the thyrotropin releasing factor is $10^{-6}$M. In one embodiment, the concentration of the HDL is 5 ug/ml. In one embodiment, the concentration of the hydrocortisone is $10^{-6}$M.

In one embodiment, the media is IM-HDM media, which comprises DMEM (high glucose), 500 ug/ml BSA, 7.6 uEq/L free fatty acids (FAA), 5 ug/ml HDL, 5 mM nicotinamide, 1× trace elements [$1\times10^{-7}$M copper, $5\times10^{-11}$M zinc, $3\times10^{-10}$M selenium], 100 ng/ml EGF, 10 ng/ml insulin, 5 ug/ml transferrin, $10^{-6}$M hydrocortisone, 2 ug/ml glucagon, 20 ug/ml liver growth factor, $10^{-6}$M ethanolamine, $10^{-6}$M thyrotropin releasing factor]. In one embodiment, the 7.6 uEq/L of total FFAs comprises a mixture 2.3604 palmitic acid (16:0), 0.21 uM palmitoleic acid (cis-16:1 n-7), 0.88 uM steric acid (18:0), 1.02 uM oleic acid (cis-18:1 n-9), 2.71 uM linoleic acid (cis-18:2 n-6), and 0.43 uM linolenic acid (cis 18:3 n-3). The media can also comprise antibiotics to deter bacterial growth, for example, 1× penicillin/streptomycin.

The cell mixtures of the compositions of this invention can be plated on plastic substrates coated with extracellular matrix. Examples of extracellular matrix components include, but are not limited to collagen, such as, for example, collagen Type IV, or the adhesion proteins, fibronectin and laminin, or Matrigel (ICN Biochemicals Inc.). The collagen, when employed, can be used alone or in combination with laminin or fibronectin, or in combination with proteoglycans, or with tissue extracts enriched in extracellular matrix materials. Extracellular matrixes can also be provided by the feeder cells describe above. Such cellular mixtures and extracellular matrix combinations can be used in HCV assay methods according to this invention.

The compositions of this invention can be contacted with RNA898 or an HCV infectious equivalent of RNA898. An RNA898 infectious equivalent is an HCV strain, other than RNA898 that is capable of producing greater than about 5,000 copies, greater than about 10,000 copies or greater than about 50,000 copies of HCV RNA at seventy-two hours after contacting $4 \times 10^5$ cells of the compositions prepared according to the methods of this invention with said HCV virus. According to one embodiment, the cells are infected by contacting the composition of this invention with RNA898 or its infectious equivalent for about 24 hours at about 37 degrees C. in a volume of about 0.52 ml per cm². According to one embodiment of this invention, the cells being infected with HCV are cultured with an extracellular matrix. In another embodiment of this invention, the extracellular matrix is provided by feeder cells (e.g., STO-(Reid-99) cells).

The amount of HCV produced from the cells in the compositions of this invention can be determined by measuring, e.g., HCV protein or nucleic acid production. For example, the number of copies of HCV RNA found associated with the cells (i.e., in or attached thereto) and/or in the media in which the cells are cultured can be quantified. There are techniques known in the art that can be used for observing whether HCV protein or nucleic acid molecules have been produced. For example, western blot of the proteins probed with antibodies directed against HCV proteins or blots of gels probed labeled nucleic acids molecules that are complementary to HCV nucleic acid sequence. Methods for extracting protein and nucleic acid molecules from cells and cell culture media are well known in the art and such kits for this purpose are commercially available.

For quantifying with greater accuracy the number of copies of HCV particles produced according to this invention, reverse-transcriptase polymerase chain reaction (RT-PCR) is useful. According to one embodiment of this invention, the RT-PCR method is modified such that the number of copies of HCV RNA are determined by comparing its value to a second nucleic acid molecule of known amount that is added to the samples of cells, cell extracts and/or media to be assayed either in the form of a second virus or a second nucleic acid molecule. It is desirable that the second virus is closely related to HCV or that the second nucleic acid molecule is closely related to HCV RNA (i.e., similar in length, in nucleic acid composition and in viral capsid structure). In one embodiment, the second nucleic acid molecule is in a flavivirus capsid. In one embodiment, the second RNA molecule is the RNA from Bovine Viral Diarrhea Virus ("BVDV"), e.g., the BVDV NADL strain (ATCC Deposit No: VR-534).

The presence of the second virus or nucleic acid molecule is advantageous in that it serves as an internal control for the quantification of the first nucleic acid molecule. This internal control allows for the monitoring and correction of random fluctuations and assay variability.

For example, the present invention provides the method comprising the steps of:
(a) combining said HCV with a known amount of Bovine Viral Diarrhea Virus ("BVDV"), wherein said BVDV contains a second nucleic acid molecule with a composition of this invention;
(b) extracting from the cells of the composition or the media in which the cells are cultivated a first nucleic acid molecule derived from HCV and said second nucleic acid molecule derived from BVDV to form a combined nucleic acid extract;
(c) adding to said combined nucleic acid extract a first detectable probe, which is specific for said first nucleic acid and a second detectable probe, which is specific for said second nucleic acid;
(d) amplifying said combined nucleic acid extract by PCR means;
(e) quantifying at various cycles during said amplification a detectable signal released independently from said first detectable probe and said second detectable probe;
(f) extrapolating the results of step (e) to calculate the amount of said first nucleic acid molecule in said HCV and the amount of said second nucleic acid molecule in BVDV; and
(g) evaluating the accuracy of said calculated amount of said first nucleic acid molecule determined in step (f) by comparing said calculated amount of said second nucleic acid in step (f) with said known amount of said second nucleic acid used in step (a).

According to another embodiment, the above method comprises the additional step of adjusting said calculated amount of said first nucleic acid determined in step (f) by a factor determined by comparing said calculated amount of said second nucleic acid in step (f) with said known amount of said second nucleic acid used in step (a).

According to another embodiment, the present invention provides a method of determining the affect of a compound on the production of an HCV, comprising the steps of adding a compound before or after administering the HCV to the compositions of this invention and subsequently determining the presence of HCV associated with the cells in the compositions and/or media in which the infected cells are cultivated. If it is desired that the compound is administered after the HCV is contacted with the composition, then it is preferable that the compound be administered within 10 days after the HCV is contacted with the composition. The compounds to be tested according to this invention can inhibit or activate the production of HCV. Accordingly, a compound can inhibit any stage of the life cycle of the HCV to achieve its effect. Examples of such compounds include, but are not limited to, synthetic or purified chemical compounds, proteins and nucleic acid molecules. The samples to which the compounds were added can be compared to other samples treated under the same conditions but have not been exposed to the compound or have been exposed to another compound that is known to have little or no effect on HCV production.

According to one embodiment, the above method is used to simultaneously screen the affect of a plurality of compounds on HCV production. For example, each well of a 96-well plate could contain a different compound to be screened according to the methods of this invention. In a further embodiment, the methods of this invention are used to identify compounds that inhibit the production of HCV.

In one embodiment, the primers and probe used in the methods of this invention are designed based upon most conserved regions of HCV strains. The probe can also be constructed based upon the following additional criteria: a) the melting temperature of the probe is 8° C. to 10° C. higher than that of the primers; b) no G's are present at the 5' end; c) there is not a stretch of more than 4 G's; and/or d) the probe does not form internal structures with high melting temperatures or form a duplex with itself or with any of the primers. In one embodiment, the entire PCR region was about 150 base pairs in length.

Useful primers and probe for the 5' UTR of BVDV can be designed based on the same set of criteria. In addition, care was taken to ensure that the primers or probe of HCV has the least amount of homology to those of BVDV. Primers and probes can be obtained from commercial sources that synthesize and prepare modified nucleic acid molecules (e.g, Oligo and PE Applied Biosystems). BVDV can be maintained by infection of MDBK cells.

In one embodiment of the invention, two different dual-labeled fluorogenic probes are used, each specific for one but not the other of the HCV nucleic acid molecules and the second nucleic acid molecules. In a further embodiment, each fluorogenic probe typically has a reporter dye at the 5'-end and a quencher dye at the 3' end. The two different fluorogenic probes are selected such that they give distinct fluorescence peaks that can be detected without cross-interference between the two peaks. For example, as discussed supra, the 5' end of the first detectable probe can be labeled with a reporter dye such as 6-carboxy-fluorescein ("6-FAM"), and the 5' end of the second detectable probe can be labeled with a reporter dye such as VIC. The 3' end of both detectable probes can be labeled with a quencher dye such as 6-carboxymethyl-rhodamine ("6-TAMRA"). Thus, when bound to the first nucleic acid and the second nucleic acid, the proximity of the reporter dye at the 5' end to the quencher dye at the 3' end of the probe results in a suppression of the fluorescence. During amplification, when the Tth polymerase moves along the nucleic acid sequence, the quencher is removed from the probe by the action of the 5'-3' exo, thereby degrading the fluorogenic probe. This results in a fluorescence emission, which is recorded as a function of the amplification cycle. Thus, monitoring the fluorescence emission provides a basis for measuring real time amplification kinetics.

Examples of useful primers and probes for HCV genotype 1 are: (SEQ ID NO:1) 5'-CCATGAATCACTCCCCTGTG-3' (forward primer), (SEQ ID NO:2) 5'-CCGGTCGTCCTG-GCAATTC-3' (reverse primer), and the HCV probe, (SEQ ID NO:5) 5'-6-FAM CCTGGAGGCTGCACGACACTCA-TAMRA-3'. The primers and probe for BVDV comprised the forward primer, (SEQ ID NO:3) 5'-CAGGGTAGTCGT-CAGTGGTTCG-3', the reverse primer, (SEQ ID NO:4) 5'-GGCCTCTGCAGCACCCTATC-3', and the probe, 5'-VIC (SEQ ID NO: 6) CCCTCGTCCACGTG-GCATCTCGA-TAMRA-3'.

The RT and the PCR reactions can be carried in the same wells of a 96 well plate optical tray with caps (PE Applied Biosystems, Foster City, Calif.). In one embodiment of this invention, a multiplex RT-PCR reaction is used (i.e., a RT-PCR reaction that amplifies and measures two different RNA species simultaneously, e.g., HCV RNA and BVDV RNA, in the same tube). The multiplex reactions has the advantage of allowing the practitioner to determine if an HCV negative result was due to the fact that the culture was truly negative or some technical failure in the extraction or RT-PCR steps. Ten or twenty ul of viral RNA or RNA standard can be amplified in a 50 ul RT-PCR reaction with 1× Taqman EZ buffer (PE Applied Biosystems), 3 mM manganese acetate, 300 mM each of dATP, dCTP, dGTP, and dUTP, 5 units Tth polymerase (Epicentre), 4.0% enhancer (Epicenter), some concentration of probes and primers. The Taqman RT-PCR assay can be run for 25 min at 60° C. (RT), 5 mM at 95° C., and followed by 45 cycles of two-step PCR reaction (60° C. for 1 min and 95° C. for 15 sec). For an assay with HCV and another nucleic acid (the multiplex Taqman assay), the amount of HCV and BVDV primers can be optimized using a matrix mixture of various concentration of both sets of primers. The final assay condition includes 200 nM of both 6-FAM-labeled HCV probe and VIC-labeled BVDV probe, 400 nM of both HCV primers, and 45 nM of both BVDV primers.

Throughout the specification and claims, the word "comprise," or variations such as "comprises" or "comprising," will be understood to imply the inclusion of a stated integer or group of integers but not the exclusion of any other integer or group of integers.

U.S. provisional application 60/279,174, filed Mar. 27, 2001, and articles recited herein are incorporated by reference.

While a number of embodiments of this invention have been presented, it is apparent that the basic construction can be altered to provide other embodiments which utilize the compositions and methods of this invention. Therefore, it will be appreciated that the scope of this invention are to be defined by the claims and specification rather than the specific embodiments which are exemplified here.

Example I

Isolating and Culturing Human Fetal Liver and Hematopoietic Cells

Liver tissue from human fetuses aged 18 to 22 weeks after conception were stored in RPMI on ice prior to dissection. The tissue was washed with PBS solution. The tissue was minced by scalpel in 50 mls of dissection buffer [HBSS (Cellgro cat no 21-022-cv), 0.5 mM EGTA, 0.2 mM $MgSO_4$, 10 mM HEPES]. The minced tissue was incubated 10 minutes in a 37 degree C. water bath. The cells detached and suspended over the minced tissue were removed. The minced tissue was incubated in collagenase solution (2 m/ml collagenase (Sigma C-5138) in collagenase buffer [HBSS, 1 mM $CaCl_2$, 10 mM HEPES]) for 30 minutes at 37 degrees C. The detached cells suspended above the minced tissue were collected and passed through a 40 micron nylon filter (Falcon nos. 2034, 2350 or 2360). The minced tissue was washed with IM-wash solution [DMEM (high glucose JRH-51444), 500 ug/ml BSA (Sigma A8806), 7.6 uEq/L total free fatty acids (FAA), 1× Penn/Strep, 10 ng/ml insulin, 5 ug/ml transferrin].

The solutions containing the cells that were passed through the filters were pooled and spun at 1000 rpm for eight minutes. The supernatant was discarded. The pellet was resuspended in 50 mls of IM-wash solution and spun at 50×g (450 rpm) for 4 minutes. The supernatant was discarded. The process of resuspending the pellet in IM-wash solution, spinning the resuspension at 50×g for 4 minutes and discarding the supernatant was repeated 2-3 times. The pellet was then suspended in 20 mls of IM-HDM media [DMEM (high glucose JRH-51444), 500 ug/ml BSA (Sigma A8806), 7.6 uEq/L of free fatty acids (FFAs) [2.36 uM palmitic acid (16:0, Sigma, P0500), 0.21 uM palmitoleic acid (cis-16:1 n-7, Sigma, P9417), 0.88 uM steric acid (18:0, Sigma, S4751), 1.02 uM oleic acid (cis-18:1 n-9, Sigma, O1008), 2.71 uM linoleic acid (cis-18:2 n-6, Sigma, L1376), and 0.43 uM linolenic acid (cis 18:3 n-3, Sigma, L2376)], 5 ug/ml HDL (Sigma L2014), 5 mM nicotinamide (Sigma N0636), 1× Penn/Strep (Gibco 1×), 1× trace elements [$1×10^{-7}$M copper (C8027), $5×10^{-11}$M zinc (Sigma 4750), $3×10^{-10}$M selenium (Sigma S6663)], 100 ng/ml EGF (Peprotech 100-15), 10 ng/ml insulin (Sigma 15500), 5 ug/ml transferrin (Sigma T0665), $10^{-6}$M hydrocortisone (Sigma 15500), 2 ug/ml glucagon (Sigma G3157), 20 ug/ml liver growth factor (Sigma G1887), $10^{-6}$M ethanolamine (Sigma E0135), $10^{-6}$M thyrotropin releasing factor (Sigma T9146)].

The pelleted cells were plated in IM-HDM media at a density of $3×10^5$ cells/$cm^2$. The pelleted cells grew well on an extracellular matrix. The pelleted cells can grow on plates that have been coated with collagen. The method of Salas-Prato, *Invitro Cell. Dev. Biol* 24:230, 1988 was used to coat the plates. Generally, a plate was incubated with a collagen type I stock solution (30 ug/ml in DMEM at 37 C. for 30 minutes-1 hour, rinsed twice with PBS, covered with PBS, and stored under PBS until needed.

Alternatively, the plates can be coated with feeder cells prior to adding the pelleted cells. For example, STO(Reid-99) cells that were Mitomycin C treated were used as feeder cells. The Mitomycin C growth arrests the STO cells yet the cells remain alive and provide a surface for the liver cells to attach.

If used, STO cells were plated in 1.9 cm$^2$ wells ($1.2 \times 10^5$/well for 24-well plates, $2.2 \times 10^4$/well for 96-well plates) in normal STO medium (RPMI-1640, 10% FCS) and allowed to adhere for 2-48 hours. The media was removed and replaced with media containing 2 ug/ml Mitomycin C and then incubated at 37 degrees C. for 2 hours. The media was removed, the STO cells were washed twice with normal STO medium, and the cultures are maintained from 0-48 hours before addition of fetal cells.

After 24-48 hours, non-attached fetal cells were removed using gentle pipetting. The media is generally changed every 2-7 days. The cells have been maintained at least 28 days with solid cell attachment and good cell morphology.

Immunostaining of the cell mixture was performed in wells of 24-well plates or 96-well plates at day 11 after infection with HCV. Alpha-1-Fetoprotein antibody and negative control antibody were obtained from DAKO Corporation (DAKO), Carpinteria, Calif. Anti-human CD34 (34371A) and anti-glycophorin (32591A) mouse monoclonal antibodies were obtained from PharMingen, San Diego Calif. and used with mouse negative control (N1537) antibody from DAKO. Staining was performed using the LSAB2 or K0676 (alkaline phosphatase) kit of DAKO according to the manufacturer's instructions. The immunostaining indicated that the cell mixture has cells that express alpha fetoprotein, cells that express glycophorin, cells that express albumin, but does not have cells that express CD34.

Example 2

HCV Infection

Ninety-six or 24-well plates were coated with the STO (Reid-99) feeder cells of Example 1. The cells prepared as described in Example 1 were plated over the STO(Reid-99) cells in the 24-well plate. The cells were infected with $9.3 \times 10^6$ Chiron bDNA Eq/ml titer of hepatitis C virus, RNA898, per well purchased from ProMed Dx. The inocula were selected so as to make the final concentration in the well 20%-30% of added serum, or $1.2 \times 10^6$ to $2.8 \times 10^6$ Chiron bDNA Eq/ml. HCV infection and replication was generally observed over a period of 20 days. During the incubation before assaying the HCV production, the media was replaced every 2-3 days. The amount of HCV infection and replication was quantitated by measuring the number of copies of the HCV RNA in the cells and media by RT-PCR.

RT-PCR Assay

HCV RNA was extracted from the cells by using the Rneasy-96 method or from cell culture supernatants using QIAamp 96 Extraction method (reagents from Qiagen, Valencia Calif.). Both procedures employ small-scale isolation and concentration of viral RNA using a chaotropic agent together with silica glass, which is capable of binding nucleic acids in presence of chaotropic salt. Bovine Viral Diarrhea Virus (BVDV) is added as to the cell lysates (approximately $10^6$ BVDV copies/sample) before the chaotropic solution is added. Glass fiber columns are arranged in a 96-well format. The nucleic acid molecules are eluted with RNase-free water into the wells (approximately 70-100 uls). BVDV was originally obtained from the ATCC (ATCC Deposit No: VR-534). The BVDV control was constant from assay to assay using these protocols.

Multiplex RT-PCR reactions, i.e., those RT-PCR reactions that amplify and measure two or more different RNA species simultaneously, in the same tube, were used for these experiments. The HCV RT-PCR assay used herein was sensitive to less than 10 copies per reaction and linear over a range from 100 to $10^7$ copies. Ten to twenty ul of extracted HCV RNA sample was tested in each RT-PCR assay.

RT-PCR was performed using the following reagents, EZ RT-PCR core reagent kit (Applied Biosystems); 3 mM manganese acetate; 300 uM each of dATP, dCTP, dGTP, dUTP; 400 nM HCV forward primer (SEQ ID NO:1) 5'-ccatgaatcactccctgtg-3; 400 nM HCV reverse primer (SEQ ID NO:2) 5'-ccggtcgtcctggcaattc-3; 45 uM BVDV forward primer (SEQ ID NO:3) 5'-cagggtagtcgtcagtggttcg-3; and 45 uM BVDV reverse primer (SEQ ID NO:4) 5'-ggcctctgcagcaccctatc-3', and 0.1 U/ul of Tth polymerase (Epicentre). DNA oligos tagged with a dye and containing nucleic acid sequence derived from HCV RNA and BVDV RNA were used as probes for the nucleic acid products generated from the RT-PCR (i.e., 200 uM FAM HCV probe (SEQ ID NO:5) 5'-FAM cctggaggctgcacgacactca-TAMRA-3' and 200 uM VIC BVDV probe (SEQ ID NO: 6) 5'-VIC-ccctcgtccacgtg-gcatctcga-TAMRA-3'). The reverse transcriptase and polymerase chain reactions were carried out in the same well in a ABI 7700 thermal cycler (Applied Biosystems). An RT-PCR assay was performed on a set of known amounts of HCV RNA simultaneously with the samples were being assayed by RT-PCR and a standard curve was generated from those results.

For each experiment, the limit of quantitation was determined. The limit of quantitation is determined by measuring the lowest concentration of RNA that, after extraction and analysis in the RT-PCR procedure, produces an output value that is within the linear portion of the standard curve. Generally, all the negative controls (i.e., demonstrating little or no HCV production) should be below the LOQ.

Fluorescence was measured with an ABI 7700 Sequence Detector (Applied Biosystems). The presence of the control RNA, BVDV, in all samples confirms that the RNA extraction and RT-PCR steps of the assay were successful. The BVDV result was positive. Thus, it was possible to interpret a negative HCV result with confidence.

Example 3

Time Course Analysis of the HCV in Culture Media after Infection

Cultures of human fetal cells were prepared as described in Examiner 1 and plated over a feeder layer of Mytomycin C treated STO(Reid-99) cells. The number of cells plated were $2 \times 10^5$/well. Sera from a human patient infected with HCV (RNA898) was purchased from ProMed Dx. As a control, no serum as added to another sample of cells to be tested. A 300 uls aliquot of HCV patient sera was added to a separate 0.7 ml of culture medium. The cultures were incubated with the virus for 24 hours at 37 degrees C. The innoculum was removed, the cultures were washed with 1 ml of medium, and then cultured in fresh medium. Culture supernatants were sampled before each medium change (every 2-3 days) and HCV RNA measured using a quantitative multiplex HCV specific RT-PCR assay as described in Example 2. The limit of quantitation (----LOQ) of the RT-PCR assay for supernatant samples was 600 HCV RNA copies/sample.

FIG. 1 depicts the results of the RT-PCR assay of the cell culture supernatant. FIG. 1 shows that RNA898 showed evidence of high infection. The negative control serum yielded no HCV RNA production. All negative controls were below the LOQ.

Example 4

Time Course Analysis of the HCV in Culture Media after Infection

Cultures of human fetal cells were prepared as described in Example 1 and plated over a feeder layer of Mytomycin C treated STO(Reid-99) cells. The number of cells plated were $4 \times 10^5$/well. Sera from a human patient infected with HCV (RNA898) and not infected with HCV was purchased from ProMed Dx (negative control serum). A 200 ul aliquot of HCV patient sera was added to a separate 0.8 ml of culture medium. This represents approximately $1.9 \times 10^6$ Chiron bDNA Eq/well. The cell culture was incubated with the virus for 24 hours at 37 degrees C. The inoculum was removed, the cultures were washed with 1 ml of medium, and then cultured in fresh medium. Culture supernatants were sampled before each medium change (every 2-3 days) and HCV RNA measured using a quantitative multiplex HCV specific RT-PCR assay as described in Example 2. The limit of quantitation (----LOQ) of the RT-PCR assay for supernatant samples was 600 HCV RNA copies/sample.

Figure 2:
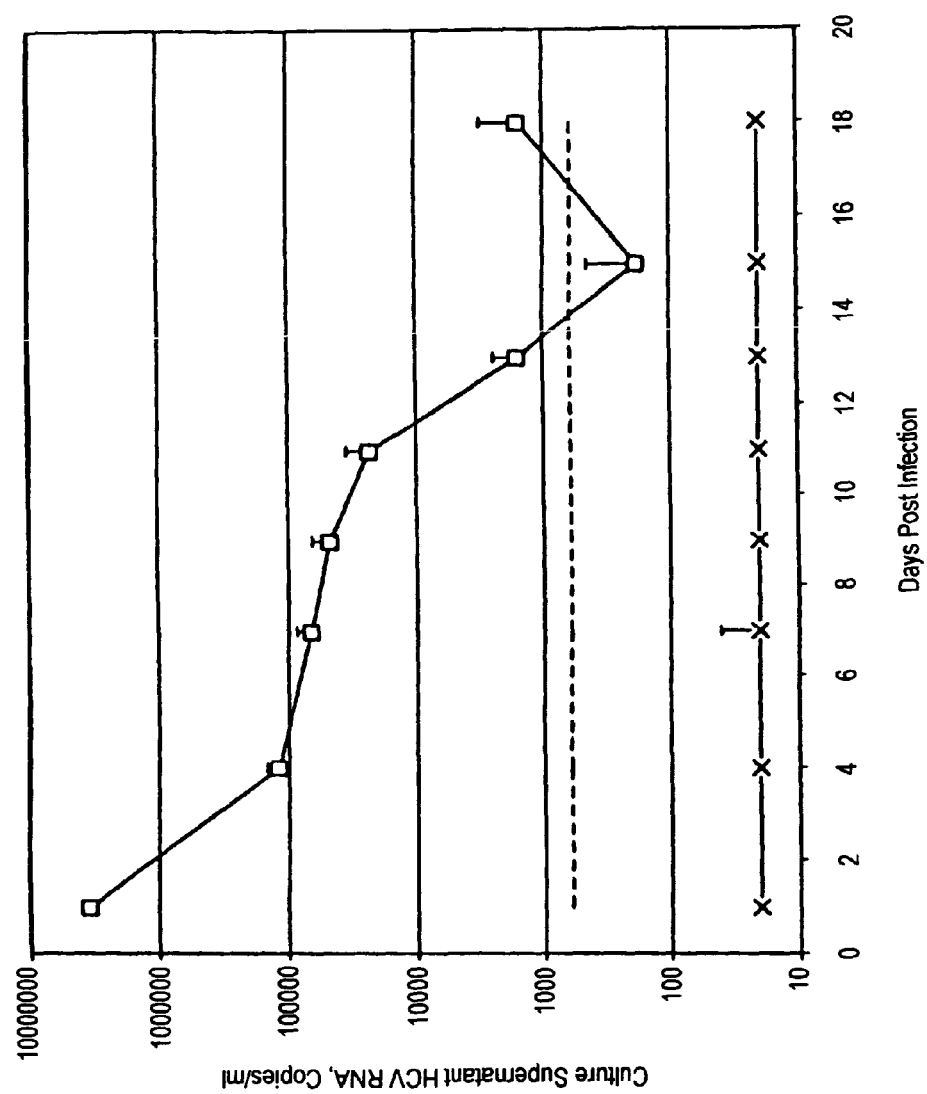
FIG. 2 depicts a time course analysis of the infection of human fetal liver cells following infection with RNA898 (-□-) or a negative control serum (-X-) as measured by levels of HCV RNA present in culture supernatants. The negative control serum was obtained from a patient not suffering from HCV infection. The limit of quantitation (----LOQ) of the RT-PCR assay for supernatant samples was 600 HCV RNA copies/sample. The mean HCV RNA/ml values, and their standard deviation, from triplicate cultures are presented.
Figure 3:
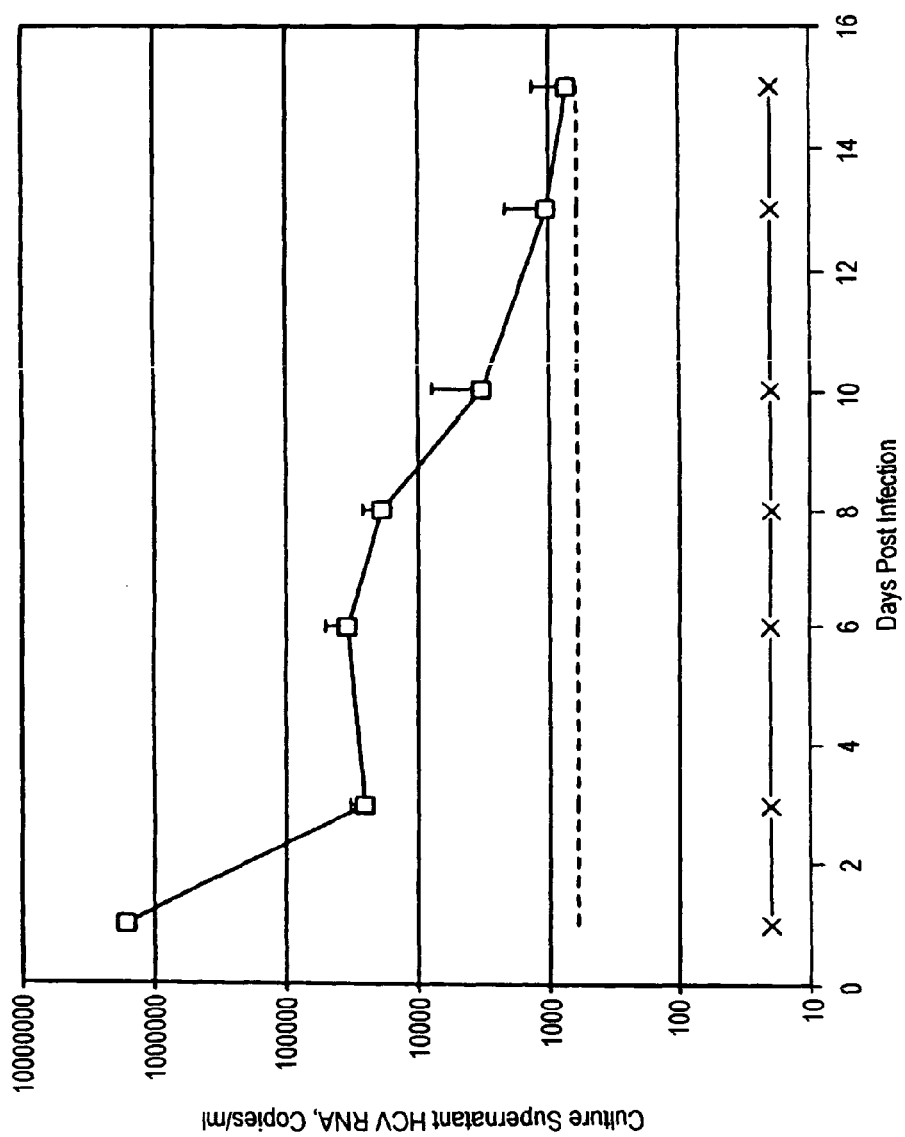
FIG. 3 depicts a time course analysis of the infection of human fetal liver cells following infection with RNA898 (-□-) or a negative control serum (-X-) as measured by the levels of HCV RNA present in the culture supernatants. The negative control serum was from a patient not suffering from HCV infection. The limit of quantitation (----LOQ) of the RT-PCR assay for supernatant samples was 600 HCV RNA copies/sample. The mean HCV RNA/ml values, and their standard deviation, from triplicate cultures are presented.

FIG. 2 and FIG. 3 depict the results of the RT-PCR assays of the cell culture supernatants. RNA898 showed evidence of high infection. The negative control culture showed no HCV RNA production. FIGS. 2 and 3 are examples of the high level of reproducibility of this HCV assay, not obtainable using similar HCV assays.

Example 5

Time Course Analysis of Cell Associated HCV RNA after HCV Infection

Cultures of human fetal cells were prepared as described in Example 1 and plated over a feeder layer of mytomycin C treated STO(Reid-99) cells. The number of cells plated were $4 \times 10^5$/well. This represents approximately $1.9 \times 10^6$ Chiron bDNA Eq/well. A 200 ul aliquot of serum RNA898 (or negative control serum, not shown) was added to 0.8 ml of culture medium. The culture was incubated with the virus for 24 hours at 37° C. The inoculum was removed, the cultures were washed twice with 1 ml of IM-wash media, and then the cultures were either fed with fresh IM-HDM medium or harvested by disruption with lysis buffer. Cultures were similarly washed, then fed or harvested on day 2, day 3, day 6, and day 8 after infection. The total RNA was extracted from the stored lysates using the Rneasy method (Qiagen). HCV RNA in the samples was measured using a quantitative multiplex HCV specific RT-PCR assay. The limit of quantitation (----LOQ) of the RT-PCR assay for cell associated RNA samples was 100 HCV RNA copies/sample. All negative control cultures showed no HCV RNA (data not shown).

Figure 4:
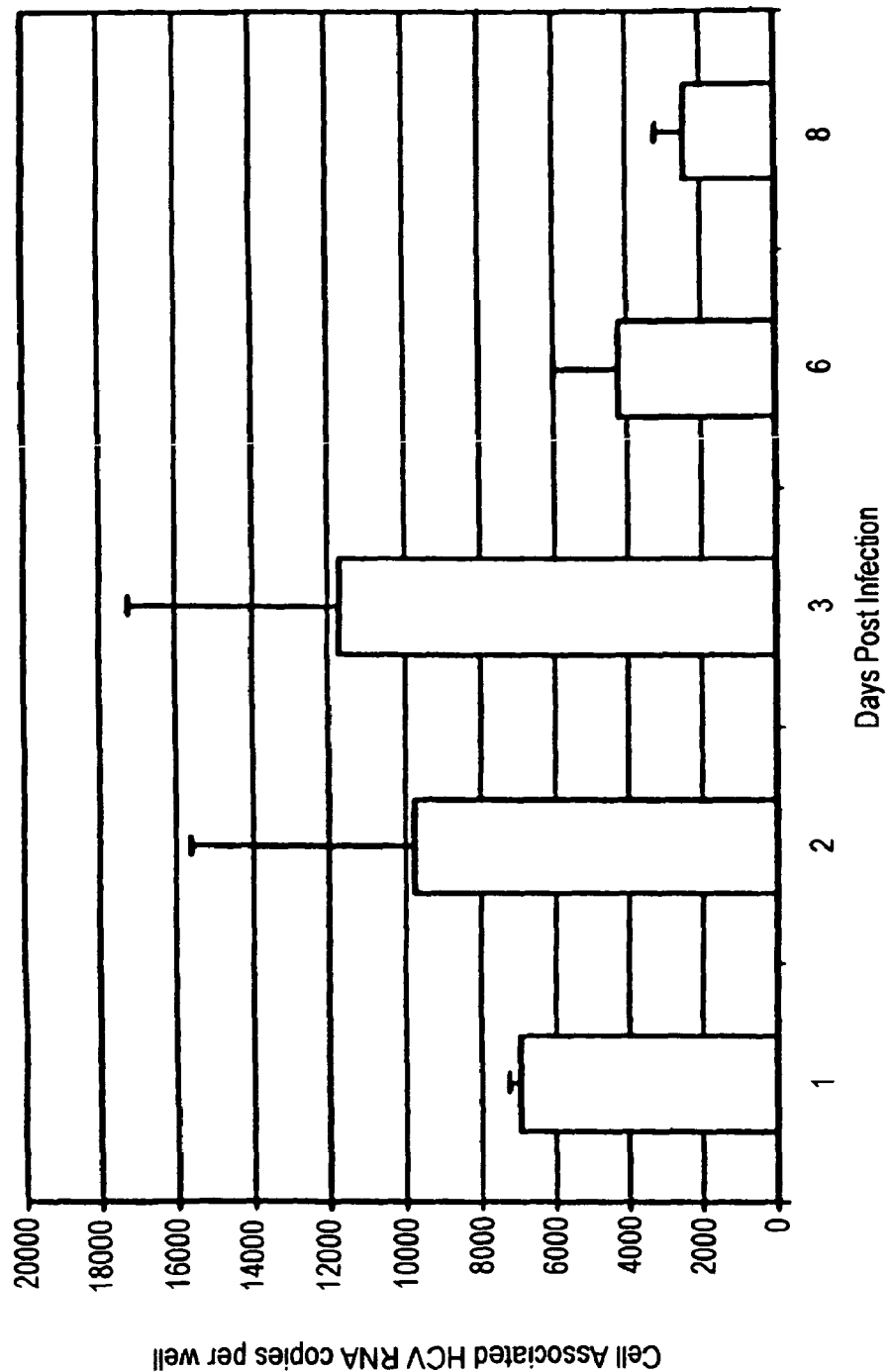
FIG. 4 depicts a time course analysis of the infection of human fetal liver cells following infection with RNA898, as measured by the levels of cell associated HCV RNA. The negative control serum data is not shown. After innoculation, the cells in the cultures were washed and harvested on days 1, 2, 3, 6 and 8 after administration of the virus. The limit of quantitation (----LOQ) of the RT-PCR assay for cell-associated RNA samples was 100 HCV RNA copies/sample. The mean HCV RNA/well values, and their standard deviation, from triplicate cultures are presented.

FIG. 4 depicts the results of the RT-PCR assay of the cell-associated RNA. The highest levels of cell-associated HCV RNA were observed on days 2 and 3 after infection and significant HCV RNA was still present day 6 after infection. The increase in HCV RNA from day 1 to day 3 occurred after removal of the external inoculum, thus indicating the HCV is replicating within the cells.

Example 6

Inhibition of HCV Infection of Human Fetal Liver Cells by the Antiviral Agent VRT-106866

Cultures of human fetal cells were prepared as described in Example 1 and plated over a feeder layer of mytomycin C treated STO(Reid-99) cells. The number of cells plated were $4 \times 10^5$/well. A 200 ul aliquot of serum RNA898 (or negative control serum, not shown) were added to 0.8 ml of culture medium and incubation performed for 24 hours at 37° C. After 24 hours, the media was removed, the cultures were washed, and the culture medium replaced with IM-HDM containing different concentrations of the compound VRT-106866 (from 0 to 10 uM). Each inhibitor concentration was tested in triplicate and the positive control (no inhibitor) was performed in sextuplicate. After incubation for 48 hours in the presence of inhibitor, the supernatants were removed and replaced with fresh medium containing the same concentration of inhibitor. After an additional 3 days, the culture medium was removed, the cultures were washed, and the cell monolayer was disrupted with lysis buffer and total RNA extracted using the Rneasy method (Qiagen) as described in Example 2. HCV RNA in the samples was measured using a quantitative multiplex HCV specific RT-PCR assay. The limit of quantitation of the RT-PCR assay for cell associated RNA samples was 100 HCV RNA copies/sample.

Figure 5:
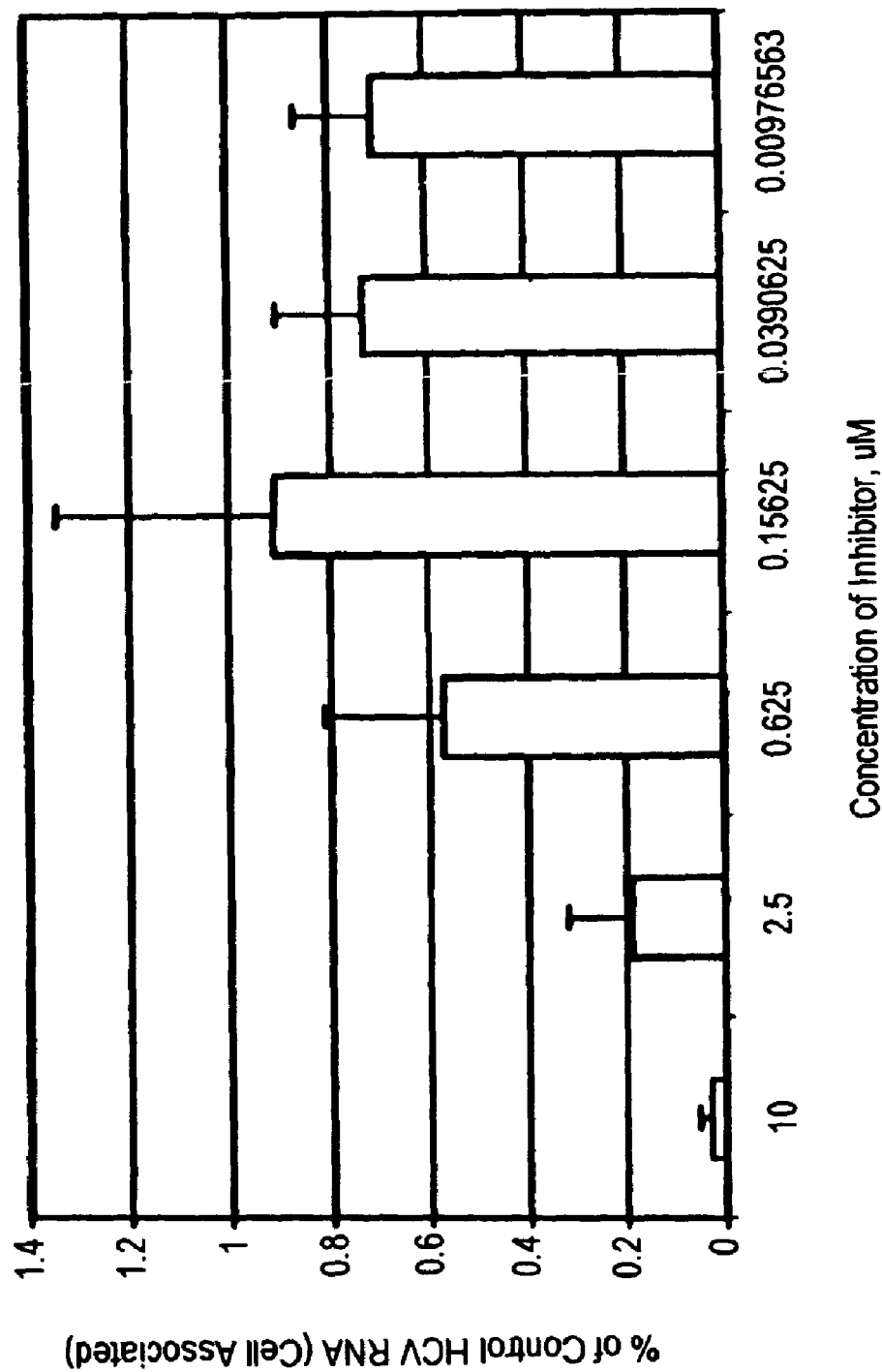
FIG. 5 depicts the inhibition of HCV infection of human fetal liver cells by the antiviral agent VRT-106866 over a concentration range. HCV RNA in the samples was measured using a quantitative multiplex HCV specific RT-PCR assay. The limit of quantitation of the RT-PCR assay for cell associated RNA samples was 100 HCV RNA copies/sample. The results are presented as mean and standard deviation of "% of control HCV RNA" (sample value/mean of positive control values) from the triplicate cultures.

FIG. 5 graphically depicts the results which are presented as mean and standard deviation of "% of control HCV RNA" (sample value/mean of positive control values) from the triplicate cultures. FIG. 5 shows that VRT-106866 is an effective inhibitor of HCV infection.

We claim:

1. A method for infecting cells with Hepatitis C Virus (HCV) comprising the step of contacting a composition comprising a cell mixture comprising liver cells and hematopoietic cells, the cells being released from the liver of a human aged three months or older after conception up to 1 year after birth, with the HCV virus RNA898 ("RNA 898" deposited on Mar. 27, 2001, in the American Type Culture Collection, 10801 University Boulevard, Manassas, Va. 20110-2209; ATCC Deposit No.: PTA-3237).

2. The method according to claim 1, wherein the HCV virus is added to the composition and incubated for about 24 hours at about 37° C. in a volume of about 0.52 ml per cm² prior to washing the cells in the composition.

3. The method according to claim 1, wherein the composition further comprises a feeder cell, wherein the feeder cell is capable of providing an extracellular matrix and diffusible factors.

4. The method according to claim 1, wherein each component of the cell mixture has a size that allows it to pass through a 40-micron filter, and the cell mixture also comprises cells that express alpha fetoprotein, cells that express albumin, and cells that express glycophorin, but is free of detectable cells that express CD34 protein.

5. The method according to claim 4, wherein the presence of any CD34 protein is detected by immunofluorescence or immunoperoxidase staining.

6. The method according to claim 1, wherein each component of the cell mixture has a size that allows it to pass through a 40-micron filter, and wherein the composition further comprises an extracellular matrix or a feeder cell, wherein the feeder cell is capable of providing an extracellular matrix and diffusible factors.

7. The method according to claim 1, wherein the composition further comprises a serum-free media, said serum-free media comprising calcium, free fatty acids (FFAs), high density lipoprotein (HDL), nicotinamide, trace elements, epidermal growth factor (EGF), insulin, transferrin, hydrocortisone, and, optionally, any one of the ingredients selected from the group consisting of glucagon, liver growth factor, ethanolamine and thyrotropin releasing factor or any combination of them.

8. The method of claim 7, wherein the serum-free media does not comprise low density lipoprotein (LDL).

9. The method of claim 1, wherein the composition being prepared by the following steps:
  a. dissecting a liver of a human aged three months or older after conception up to 1 year after birth in a buffer comprising ethylene glycol bis (β-aminoethyl ether)-N,N,N',N'-tetraacetate (EGTA);
  b. incubating the dissected liver in a buffer comprising collagenase to separate cells from the liver;
  c. passing the separated cells through a 40-micron filter;
  d. removing red blood cells from the filtered cells;
  e. resuspending the cells of step (d) in serum-free media, comprising calcium, FFAs, HDL, nicotinamide, trace elements, EGF, insulin, transferrin, hydrocortisone, and optionally, further comprising any one of the ingredients selected from the group consisting of: glucagon, liver growth factor, ethanolamine and thyrotropin releasing factor or any combination of them; and
  f. culturing the cells in the serum-free media of step (e).

10. The method according to any one of claims 1, 2 and 3-9, wherein the method produces more than 5,000 copies of HCV RNA seventy-two hours after administering RNA 898 to $4 \times 10^5$ of said cells.

11. The method according to any one of claims 1, 2 and 3-9, wherein the method produces more than 10,000 copies of HCV RNA seventy-two hours after administering RNA 898 to $4 \times 10^5$ of said cells.

12. The method according to any one of claims 1, 2 and 3-9, wherein the method produces more than 50,000 copies of HCV RNA seventy-two hours after administering RNA 898 to $4 \times 10^5$ of said cells.

* * * * *